(12) United States Patent
Ruiz et al.

(10) Patent No.: US 8,496,651 B2
(45) Date of Patent: *Jul. 30, 2013

(54) SYSTEM AND METHOD FOR REFRACTIVE SURGERY WITH AUGMENTATION BY INTRASTROMAL CORRECTIVE PROCEDURE

(75) Inventors: Luis Antonio Ruiz, Bogotá (CO); Frieder Loesel, Mannheim (DE); Josef F. Bille, Heidelberg (DE)

(73) Assignee: Technolas Perfect Vision GmbH, Munich (DE)

( * ) Notice: Subject to any disclaimer, the term of this patent is extended or adjusted under 35 U.S.C. 154(b) by 1194 days.

This patent is subject to a terminal disclaimer.

(21) Appl. No.: 12/360,726

(22) Filed: Jan. 27, 2009

(65) Prior Publication Data

US 2010/0191228 A1  Jul. 29, 2010

(51) Int. Cl.
*A61B 18/18* (2006.01)

(52) U.S. Cl.
USPC .................................................. 606/5

(58) Field of Classification Search
USPC ................ 606/4–6, 161, 166; 128/898
See application file for complete search history.

(56) References Cited

U.S. PATENT DOCUMENTS

| | | | |
|---|---|---|---|
| 4,309,998 A | 1/1982 | Aron nee Rosa et al. | |
| 4,391,275 A | 7/1983 | Fankhauser et al. | |
| 4,406,285 A * | 9/1983 | Villasenor et al. | 606/166 |
| 4,669,466 A | 6/1987 | L'Esperance | |
| 4,718,418 A | 1/1988 | L'Esperance, Jr. | |
| 4,721,379 A | 1/1988 | L'Esperance | |
| 4,732,148 A | 3/1988 | L'Esperance, Jr. | |
| 4,770,172 A | 9/1988 | L'Esperance, Jr. | |
| 4,887,592 A | 12/1989 | Loertscher | |
| 4,907,586 A | 3/1990 | Bille et al. | |
| 4,941,093 A | 7/1990 | Marshall et al. | |
| 4,988,348 A | 1/1991 | Bille | |
| 5,549,632 A | 8/1996 | Lai | |
| 5,984,916 A | 11/1999 | Lai | |
| 5,993,438 A | 11/1999 | Juhasz et al. | |
| 6,110,166 A | 8/2000 | Juhasz | |
| 6,325,792 B1 | 12/2001 | Swinger et al. | |
| 6,610,051 B2 | 8/2003 | Bille | |
| 2002/0103478 A1 * | 8/2002 | Gwon et al. | 606/4 |
| 2003/0212387 A1 * | 11/2003 | Kurtz et al. | 606/4 |
| 2004/0044355 A1 * | 3/2004 | Nevyas | 606/166 |
| 2005/0085800 A1 * | 4/2005 | Lenzner et al. | 606/5 |
| 2005/0165386 A1 * | 7/2005 | Kurtz et al. | 606/4 |
| 2006/0155265 A1 * | 7/2006 | Juhasz et al. | 606/5 |

(Continued)

OTHER PUBLICATIONS

Sakimoto et al., "Laser eye surgery for refractive errors," The Lancet vol. 367, 9520 pp. 1432-1447 Apr. 29-May 5, 2006.*

*Primary Examiner* — Ryan Severson
*Assistant Examiner* — David Eastwood
(74) *Attorney, Agent, or Firm* — Nydegger and Associates

(57) ABSTRACT

A system and method are provided for an ophthalmic surgical procedure to provide a refractive correction for an eye. Specifically, the procedure is indicated when the desired refractive correction "$d_{reqd}$" exceeds the capability of a correction achievable when corneal tissue is only ablated. In accordance with the present invention, an optimized refractive correction "$d_1$" is accomplished by the ablation of corneal tissue (e.g. by a PRK or LASIK procedure). The optimized correction is then followed by a complementary refractive correction "$d_2$" wherein stromal tissue is weakened with Laser Induced Optical Breakdown (LIOB). Together, the optimized refractive correction (ablation) and the complementary refractive correction (LIOB) equal the desire refractive correction ($d_{reqd}=d_1+d_2$).

17 Claims, 2 Drawing Sheets

U.S. PATENT DOCUMENTS

2006/0173445 A1* 8/2006 Bille .................................. 606/5
2007/0185475 A1* 8/2007 Frey et al. ......................... 606/4
2008/0039825 A1* 2/2008 Lai .................................... 606/5
2010/0191229 A1* 7/2010 Bille et al. ........................ 606/5
2010/0217247 A1* 8/2010 Bille et al. ........................ 606/5
2010/0241108 A1* 9/2010 Wullner et al. ................... 606/5

* cited by examiner

US 8,496,651 B2

SYSTEM AND METHOD FOR REFRACTIVE SURGERY WITH AUGMENTATION BY INTRASTROMAL CORRECTIVE PROCEDURE

FIELD OF THE INVENTION

The present invention pertains to systems and methods for ophthalmic laser surgical procedures. More particularly, the present invention pertains to laser surgery wherein a desired refractive correction requires removal of more corneal tissue than can be efficaciously removed by a single procedure. The present invention is particularly, but not exclusively, useful for surgery wherein a removal of corneal tissue by ablation is complemented by a weakening of stromal tissue by Laser Induced Optical Breakdown (LIOB) to collectively achieve a required refractive correction for an eye.

BACKGROUND OF THE INVENTION

Presently there are several different types of procedures that can be used for performing refractive surgery on the cornea of an eye to correct vision defects. In general, these procedures can be categorized according to the kind of instrument that is used to perform the surgery (e.g. a "mechanical means" or a "laser means"). Further, within the "laser means" category, there are essentially two methodologies for altering stromal tissue that differ from each other depending on whether tissue is actually removed by photoablation, or is merely weakened by a phenomenon commonly referred to as Laser Induced Optical Breakdown (LIOB).

A removal of tissue from the cornea of an eye, when using a laser means to correct a vision defect, is typically accomplished by the photoablation of exposed corneal tissue. For example, the well-known procedures of LASIK and PRK (Photo Refractive Keratectomy) both rely on the removal of exposed tissue by photoablation. On the other hand, it is also known that tissue inside the stroma can be merely weakened to correct a vision defect. For example, the weakening of intrastromal tissue for the purpose of correcting a vision defect is disclosed and claimed in U.S. patent application Ser. No. 11/958,202 for an invention entitled "Method for Intrastromal Refractive Surgery" which is assigned to the same assignee as the present invention. More specifically, the result of weakening tissue is a redistribution of biomechanical stresses in the stroma that responds to Intra-Ocular Pressure (IOP) to reshape the cornea. It can happen, however, that neither the removal of corneal tissue, nor the weakening of stromal tissue, when performed alone, may be able to achieve the desired refractive result. Much here depends on the cause of the vision defect that needs to be corrected. Thus, there are limits to the extent of an effective refractive correction when either a weakening of stromal tissue or an actual removal of tissue are considered separately.

The inherent limitations of tissue removal procedures are primarily a result of the amount of corneal tissue that can be removed. Specifically, for the rather common visual defects of myopia, hyperopia and astigmatism, it is known that going beyond the limits set forth below can cause unwanted instabilities in the cornea. In general, the practical limits for effective refractive corrections to be achieved for the more common visual defects, by tissue removal alone, are:

| Myopia | PRK | −6 diopter limit |
|---|---|---|
| | LASIK | −8 diopter limit |
| Hyperopia | PRK | +3 diopter limit |
| | LASIK | +5 diopter limit |
| Astigmatism | PRK | 3 diopter limit |
| | LASIK | 5 diopter limit |

Also, it is known that presbyopia, in combination with the visual defects considered above, may require a refractive correction that goes beyond the limits set forth above.

On the other hand, when stromal tissue is weakened, rather than removed, refractive corrections are limited to approximately 2 or 2.5 diopter. Further, for safety reasons, any stromal tissue that is to be weakened should not be within the one hundred microns immediately anterior to Descemet's membrane and the endothelium.

With the above in mind, it is an object of the present invention to provide a system and method for making myopic/hyperopic/astigmatic corrections requiring refractive changes that go beyond the limits provided by only removing corneal tissue. Another object of the present invention is to provide a system and method for combining corneal tissue removal with an intrastromal redistribution of biomechanical stresses to achieve a predetermined refractive correction for an eye. Still another object of the present invention is to provide a system and method for both removing and weakening corneal tissue, in combination, to provide refractive corrections for an eye that are relatively easy to implement and comparatively cost effective.

SUMMARY OF THE INVENTION

A system and method are provided for performing an ophthalmic laser surgical procedure, wherein a required (desired) refractive correction for an eye necessitates removal of more corneal tissue than can be efficaciously removed by photoablation alone. It follows that the required refractive correction also necessitates a greater weakening of stromal tissue than is possible by LIOB alone. The present invention, however, recognizes that the removal of an optimal amount of corneal tissue, by ablation, can be complemented by a weakening of stromal tissue, by LIOB, to achieve a required overall refractive correction for an eye.

To begin, a required diopter refractive correction for an eye "$d_{reqd}$" is established. Typically, this is done diagnostically. Next, the maximum permissible diopter refractive correction by tissue removal (i.e. ablation) and the maximum permissible diopter refractive correction by weakening stromal tissue (i.e. LIOB) are respectively determined. Stated differently, a first maximum diopter correction for the eye "$d_{1max}$" is clinically determined. Specifically, $d_{1max}$ is the refractive correction that is achievable by removing corneal tissue from the eye. Also, a second maximum diopter correction for the eye "$d_{2max}$" is clinically determined. In this case, $d_{2max}$ is the refractive correction that is achievable by changing a biomechanical stress distribution in the stroma of the eye (i.e. a weakening of the stroma). As envisioned for the present invention, $d_{reqd}$ will be greater than $d_{1max}$. And, $d_{reqd}$ will also be greater than $d_{2max}$.

In operation, corneal tissue is first ablated to achieve a first actual (i.e. an optimized) diopter correction "$d_{1actual}$". Preferably, this is done using an excimer laser to remove corneal tissue by either a LASIK or a PRK procedure. In either case, $d_{1actual}$ (i.e. the optimized refractive correction by ablation) is equal to or less than $d_{1max}$. Then, a complementary refractive correction is performed using a pulsed femtosecond laser to weaken stromal tissue. This is done by causing a Laser Induced Optical Breakdown (LIOB) of the tissue. In this case, LIOB achieves a second actual diopter correction "$d_{2actual}$". For the present invention, $d_{2actual}$ (i.e. the complementary refractive correction) is less than $d_{2max}$. Importantly, $d_{1actual} + d_{2actual}$ equals $d_{reqd}$ ($d_{reqd} = d_{1actual} + d_{2actual}$).

As envisioned for the present invention, the photoablation of corneal tissue and the weakening of stromal tissue can be accomplished substantially simultaneously, in a same procedure. It may be preferable, however, to accomplish photoablation and weakening of tissue in separate procedures that are separated from each other by a time interval that may be as much as several weeks (e.g. three weeks). In such a case, it is most likely that the photoablation (PRK or LASIK) will be accomplished first.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
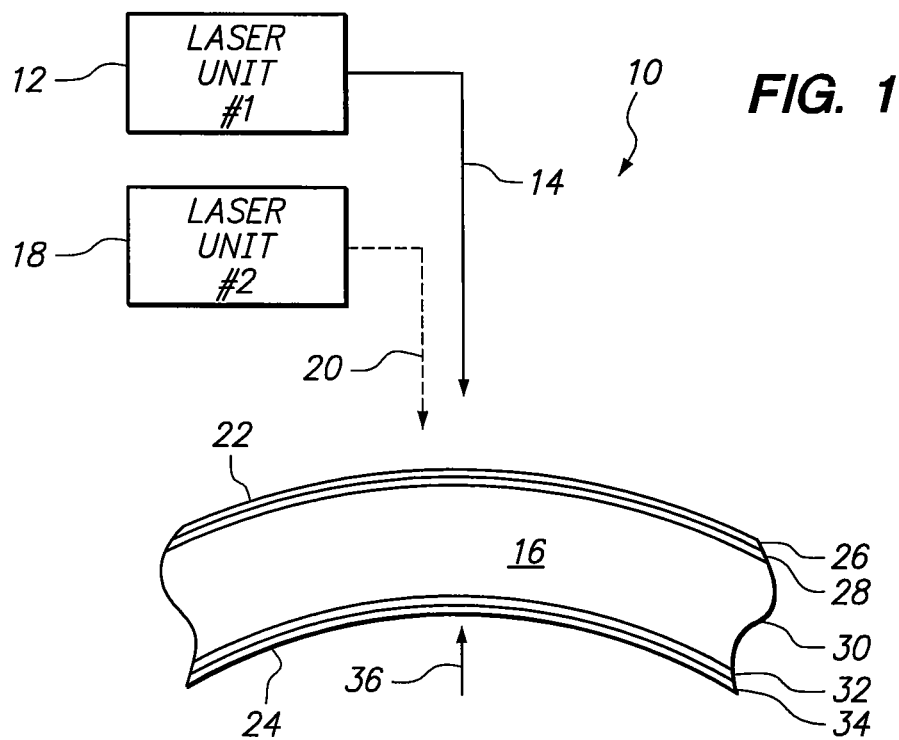
FIG. 1 is a schematic presentation of a system in accordance with the present invention shown in its operational relationship to the cornea of an eye, with the cornea shown in cross section.

Referring initially to FIG. 1 a system for use with the present invention is shown and is generally designated 10. As shown, the system 10 includes a first laser unit 12 for generating and directing a laser beam along a beam path 14 toward the cornea 16 of an eye. The system 10 also includes a second laser unit 18 for generating and directing a laser beam along a beam path 20 toward the cornea 16. For purposes of the present invention, the first laser unit 12 is of a type well known in the pertinent art that is capable of generating a laser beam for photoablating tissue of the cornea 16, such as an excimer laser. On the other hand, the second laser unit 18 is of a type that is better suited to cause the Laser Induced Optical Breakdown (LIOB) of tissue in the cornea 16. Thus, the second laser unit 18 is preferably of a type that will generate a so-called, pulsed femtosecond laser beam.

Anatomically, the cornea 16 of an eye is shown in FIG. 1 to include, in order from its anterior surface 22 to its posterior surface 24, an epithelium 26, a Bowman's membrane 28, a stroma 30, a Descemet's membrane 32, and an endothelium 34. As also shown in FIG. 1, an intra-ocular pressure (IOP) is directed against the cornea 16 from inside the eye (this IOP is represented by the arrow 36). In accordance with the present invention, the refractive properties of the cornea 16 are changed to make a desired vision correction. This is done by altering tissue in the cornea 16 through the concerted exploitation of two different mechanisms. They are: 1] actual tissue removal, and 2] a weakening of tissue. To do this, the first laser unit 12 is used for the removal of tissue from the cornea 16 by photoablation, and the second laser unit 18 is used to weaken tissue in the stroma 30 by LIOB. A consequence of both mechanisms is that the refractive power of the cornea 16 (measured in diopters) is changed. As envisioned for the present invention, a removal of tissue (photoablation), together with a weakening of the remaining tissue (LIOB), will provide a greater, more efficacious, and more beneficial change in the refractive power of the cornea 16 than can be accomplished with either mechanism alone.

Figure 2:
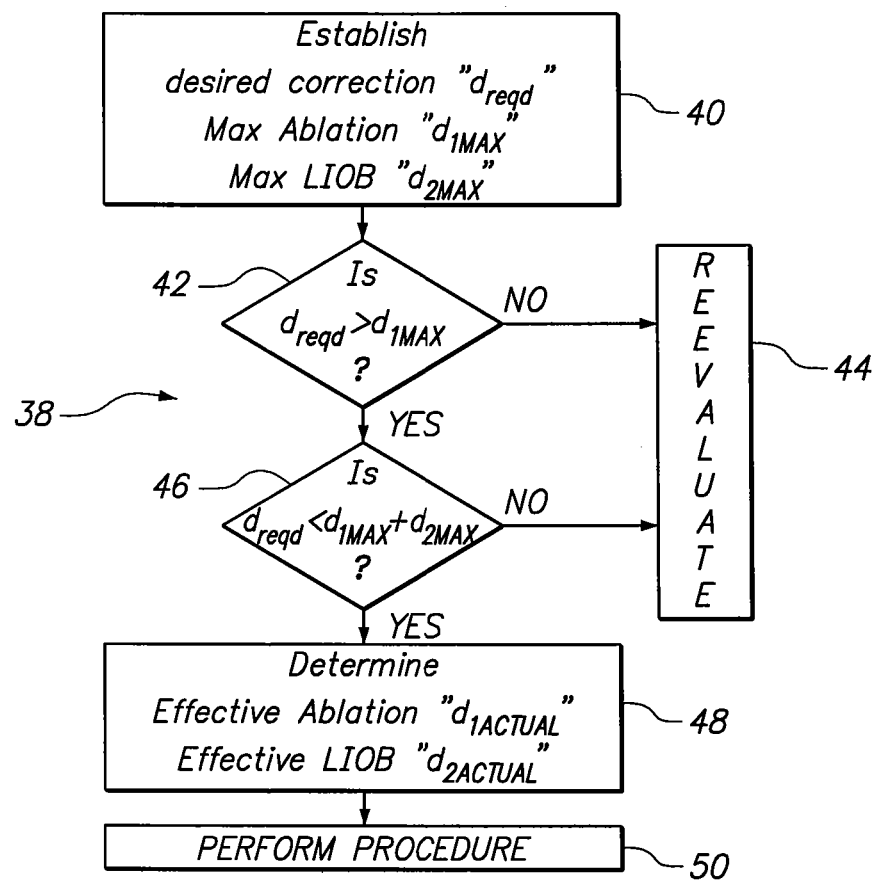
FIG. 2 is a logic flow chart for implementation of the present invention.

In FIG. 2 a methodology for implementation of the present invention is shown as a logic flow chart and is generally designated 38. There it will be seen that the initial step (represented by block 40) involves establishing certain operational parameters. Specifically, it is necessary to diagnostically determine the desired refractive correction "$d_{reqd}$" for the cornea 16. It is also necessary to ascertain the maximum permissible photoablation for removal of tissue from the cornea 16 "$d_{1max}$", and the maximum permissible weakening of the stroma 30 by LIOB "$d_{2max}$". Once these parameters have been established, inquiry block 42 indicates that the desired diopter correction "$d_{reqd}$" is to be compared with the maximum permissible photoablation correction "$d_{1max}$". If $d_{reqd}$ is less than $d_{1max}$ the procedure moves to block 44 for reevaluation. Specifically, the methodology 38 of the present invention is properly indicated when the desired (i.e. required) correction "$d_{reqd}$" is greater than could be achieved if only photoablation were used. On the other hand, as indicated by reevaluation block 44, when the maximum photoablation is sufficient (i.e. $d_{1max} > d_{reqd}$) a weakening of the stromal tissue by LIOB with the second laser unit 18 may not be necessary.

When the desired (required) refractive correction for the cornea 16 is greater than the maximum effective photoablation (i.e. $d_{reqd} > d_{1max}$), methodology 38 indicates that a subsequent inquiry is needed at inquiry block 46. Specifically, the question at this point (i.e. inquiry block 46) concerns whether the desired (required) refractive correction is less than the sum of the maximum permissible photoablation and the maximum permissible LIOB (i.e. is $d_{reqd} < d_{1max} + d_{2max}$ ?). If so, (i.e. if $d_{reqd} < d_{1max} + d_{2max}$), block 48 indicates that an effective ablation "$d_{1actual}$" and an effective LIOB "$d_{2actual}$" for refractive corrections need to be respectively determined. Block 50 then shows that the procedure is performed using "$d_{1actual}$" and "$d_{2actual}$". On the other hand, if $d_{reqd} > d_{1max} + d_{2max}$, reevaluation block 44 would indicate that a procedure should, most likely, not be performed.

Figure 3A:
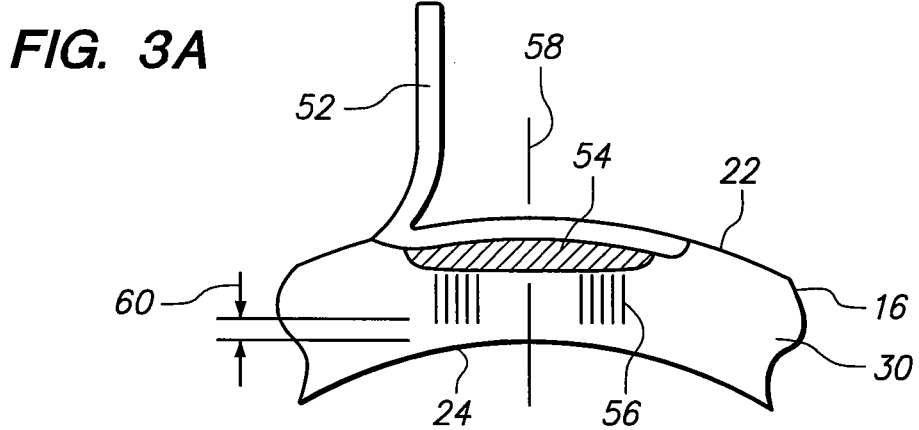
FIG. 3A is a cross section view of a cornea when the present invention involves a LASIK procedure.
Figure 3B:
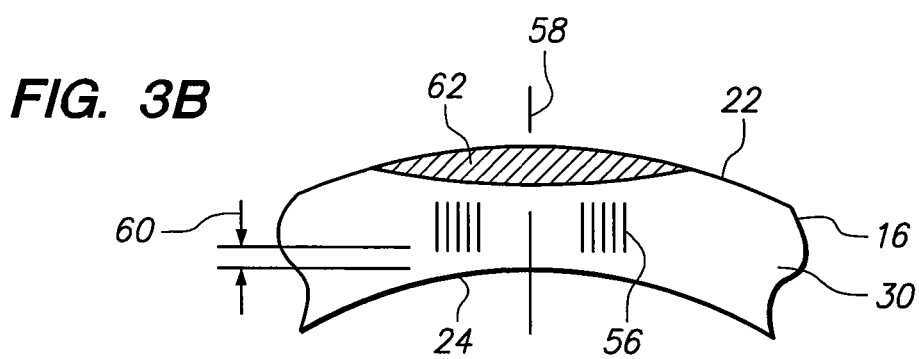
FIG. 3B is a cross section view of a cornea when the present invention involves a PRK procedure.

FIGS. 3A and 3B conceptually show the combination of the two refractive correcting mechanisms employed by the system 10 of the present invention. Specifically, FIG. 3A shows a LASIK-LIOB procedure wherein a flap 52 has been created to expose underlying tissue of the stroma 30. Once the flap 52 has been lifted, the first laser unit 12 can then be used for the photoablation (i.e. removal) of a region 54 of stromal tissue. The consequence of this is the refractive correction "$d_{1actual}$". Next, the second laser unit 18 can be used to perform LIOB that will create a series of incisions (i.e. cuts) 56 in the stroma 30 to thereby weaken the tissue. Although the incisions 56 can be made in a variety of patterns, the incisions 56 shown in FIG. 3A are considered here to be cylindrical cuts that are centered on the visual axis 58. Further, it is important that a safety distance 60 be preserved between the incisions 56 and the posterior surface 24 of the cornea 16. Preferably, this safety distance 60 is about one hundred microns. Thus, there is a weakening of tissue that will cause a redistribution of biomechanical stresses in the stroma 30, with a consequent reshaping of the cornea 16 under the influence of IOP (arrow 36). The result is the refractive correction "$d_{2actual}$", with the overall objective being that the sum of the individual refractive corrections will provide the desired (required) correction ($d_{1actual} + d_{2actual} = d_{reqd}$). Similarly, FIG. 3B shows a PRK- LIOB procedure wherein a region 62 of superficial tissue in the cornea 16 is removed by photoablation for the same purpose discussed above with reference to FIG. 3A. Again, the over all objective is that the sum of the individual refractive corrections will provide the desired (required) correction ($d_{1actual}+d_{2actual}=d_{reqd}$).

While the particular System and Method for Refractive Surgery with Augmentation by Intrastromal Corrective Procedures as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for combining corneal tissue removal with an intrastromal redistribution of biomechanical stresses to achieve a predetermined refractive correction for an eye, the method comprising the steps of:
    ablating a predetermined volume of corneal tissue to attain an optimized refractive correction for the eye ($d_1$); and
    weakening stromal tissue, by making incisions within the stromal layer below the ablated volume, to incorporate a complementary refractive correction for the eye ($d_2$) along with the optimized refractive correction, to achieve a required refractive correction ($d_{reqd}$), wherein the optimized refractive correction is less than the required refractive correction ($d_1 < d_{reqd}$).

2. A method as recited in claim 1 wherein $d_{reqd}$ is more than about 3 diopters.

3. A method as recited in claim 2 wherein $d_2$ is approximately in a range of two to two and one half diopters.

4. A method as recited in claim 1 wherein the ablating step is accomplished prior to the weakening step.

5. A method as recited in claim 1 wherein the ablating step is accomplished as a PRK procedure.

6. A method as recited in claim 1 wherein the ablating step is accomplished as a LASIK procedure.

7. A method as recited in claim 1 wherein the weakening step is accomplished using a femtosecond laser for causing Laser Induced Optical Breakdown (LIOB) of stromal tissue.

8. A method as recited in claim 1 wherein the ablating step is accomplished using an excimer laser.

9. A method for combining corneal tissue removal with an intrastromal redistribution of biomechanical stresses to achieve a predetermined refractive correction for an eye, the method comprising the steps of:
    establishing a required diopter correction for the eye "$d_{reqd}$" to achieve the predetermined refractive correction;
    determining a first maximum diopter correction for the eye "$d_{1max}$", wherein $d_{1max}$ is achievable by removing corneal tissue from the eye, and wherein $d_{reqd}$ is greater than $d_{1max}$;
    ascertaining a second maximum diopter correction for the eye "$d_{2max}$", wherein $d_{2max}$ is achievable by changing a biomechanical stress distribution in the stroma of the eye, and wherein $d_{reqd}$ is greater than $d_{2max}$;
    ablating corneal tissue to achieve a first actual diopter correction "$d_{1actual}$", wherein $d_{1actual}$ is less than $d_{1max}$; and
    performing Laser Induced Optical Breakdown (LIOB), within the stromal layer below the ablated tissue to achieve a second actual diopter correction "$d_{2actual}$", wherein $d_{2actual}$ is less than $d_{2max}$, and further wherein $d_{1actual}+d_{2actual}$ equals $d_{reqd}$ ($d_{reqd}=d_{1actual}+d_{2actual}$).

10. A method as recited in claim 9 wherein $d_{reqd}$ is more than about 3 diopters.

11. A method as recited in claim 10 wherein $d_{2max}$ is approximately in a range of two to two and one half diopters.

12. A method as recited in claim 9 wherein the ablating step is accomplished prior to the performing step.

13. A method as recited in claim 9 wherein the ablating step is accomplished as a PRK procedure.

14. A method as recited in claim 9 wherein the ablating step is accomplished as a LASIK procedure.

15. A method as recited in claim 9 wherein the performing step is accomplished using a femtosecond laser for causing Laser Induced Optical Breakdown (LIOB) of stromal tissue.

16. A method as recited in claim 9 wherein the ablating step is accomplished using an excimer laser.

17. A method as recited in claim 9 wherein the ablating step is accomplished prior to the performing step and is separated therefrom by a time interval of approximately three weeks.

* * * * *